US008858768B2

(12) United States Patent
Katsuki et al.

(10) Patent No.: US 8,858,768 B2
(45) Date of Patent: Oct. 14, 2014

(54) ELECTROCHEMICAL SENSOR AND METHOD FOR MANUFACTURING SAME

(75) Inventors: Koji Katsuki, Kyoto (JP); Yoshiaki Fujinawa, Kyoto (JP); Masashi Tsukada, Kyoto (JP); Yosuke Murase, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 576 days.

(21) Appl. No.: 13/148,465

(22) PCT Filed: Feb. 4, 2010

(86) PCT No.: PCT/JP2010/051637
§ 371 (c)(1),
(2), (4) Date: Aug. 8, 2011

(87) PCT Pub. No.: WO2010/090271
PCT Pub. Date: Aug. 12, 2010

(65) Prior Publication Data
US 2011/0308944 A1    Dec. 22, 2011

(30) Foreign Application Priority Data
Feb. 9, 2009    (JP) .................................. 2009-027246

(51) Int. Cl.
*G01N 27/327*    (2006.01)
*C12Q 1/32*    (2006.01)
*C12Q 1/00*    (2006.01)
*A61B 5/05*    (2006.01)

(52) U.S. Cl.
CPC  *C12Q 1/006* (2013.01); *C12Q 1/32* (2013.01); G01N 2333/902 (2013.01)
USPC ................ 204/403.05; 204/403.09; 600/345; 600/347

(58) Field of Classification Search
USPC ...................... 205/777.5, 778, 792; 204/403.01–403.15; 600/345, 347
See application file for complete search history.

(56) References Cited

U.S. PATENT DOCUMENTS

| | | | |
|---|---|---|---|
| 5,593,852 A | 1/1997 | Heller et al. | .................... 435/14 |
| 6,881,551 B2 | 4/2005 | Heller et al. | .................... 435/14 |
| 7,465,380 B2 * | 12/2008 | Rodgers et al. | .......... 204/403.14 |
| 2009/0101499 A1 | 4/2009 | Katsuki et al. | ........... 204/403.14 |
| 2010/0261072 A1 | 10/2010 | Tsugawa et al. | .............. 429/401 |

FOREIGN PATENT DOCUMENTS

| | | | | |
|---|---|---|---|---|
| EP | 1884771 A1 | 2/2008 | | |
| JP | 2004-294231 A | * | 10/2004 | ............. G01N 27/30 |
| JP | 2006-308463 | | 11/2006 | ........... G01N 27/327 |
| JP | 2006-322889 | | 11/2006 | ........... G01N 27/327 |
| WO | 2007/055100 A1 | | 5/2007 | |

OTHER PUBLICATIONS

Laurinavicius et al. "Wiring of PQQ-dehydrogenases," Biosensors and Bioelectronics 20 (2004) 1217-1222.*

(Continued)

*Primary Examiner* — Alex Noguerola
(74) *Attorney, Agent, or Firm* — Morgan, Lewis & Bockius LLP

(57) ABSTRACT

The present invention provides an electrochemical sensor comprising a substrate, an electrically conductive layer made of carbon particles which is disposed on the substrate, a cell membrane mimetic structure layer containing an enzyme at least one of inside the cell membrane mimetic structure layer and on the interface of the cell membrane mimetic structure layer which is disposed on the electrically conductive layer.

16 Claims, 3 Drawing Sheets

(56) References Cited

OTHER PUBLICATIONS

Mang et al., "Biocompatibility of an Electrochemical Sensor for Continuous Glucose Monitoring in Subcutaneous Tissue," Diabetes Technology & Therapeutics vol. 7, No. 1, 2005.*

JPO machine-generated English language translation of Shinbashi et al. JP 2004-294231 A downloaded Feb. 21, 2013.*

Extended European Search Report issued in corresponding European Patent Application No. 10738602.1 dated Jul. 20, 2012.

Atanasov et al., "Glucose biosensor based on carbon black strips," Biosensors & Bioelectronics, 7: 361-365 (1992).

Kudo et al., "Glucose sensor using a phospholipid polymer-based enzyme immobilization method," Analytical and Bioanalytical Chemistry, 391: 1269-1274 (2008).

International Preliminary Report in corresponding PCT/JP2010/051637 (issued Sep. 13, 2011).

* cited by examiner

ELECTROCHEMICAL SENSOR AND METHOD FOR MANUFACTURING SAME

CROSS-REFERENCE TO RELATED APPLICATION

This application is a 371 filing based on PCT/JP2010/051637, filed Feb. 4, 2010 which claims priority to Japanese Application No. JP 2009-027246, filed Feb. 9, 2009, all of which are hereby incorporated by reference in their entirety.

TECHNICAL FIELD

The present invention relates to an electrochemical sensor for measuring glucose and a method for manufacturing the same.

BACKGROUND ART

Taking advantage of the specificity of a reaction of an enzyme, an enzyme electrode (hereinafter, also referred to as biosensor) has been widely used as a sensor to specifically detect various physiologically active substances. As such an enzyme electrode, one which is constituted such that samples can be analyzed in an electrochemical method or an optical method is widely used. An enzyme electrode for analyzing samples in an electrochemical method usually refers to an electrode in which an enzyme is fixed on the surface of the electrode such as a golden electrode, platinum electrode or carbon electrode. In particular, the enzyme electrode is widely used as a glucose sensor for measuring the concentration of glucose in blood as an important marker in diabetes mellitus.

Although a basic structure of a glucose sensor and a method for manufacturing thereof is well-known, Patent Document 1 discloses a method for manufacturing a special glucose sensor. That is, Patent Document 1 discloses a technique in which the surface of an electrode substrate is modified by forming a cell membrane mimetic structure (phosphatide: 2-methacryloyloxyethyl phosphorylcholine (MPC)) on a support such as an electrode substrate. The shape of the structure of the support is not restricted, and examples thereof include a film, an inner wall of a capillary pipe, a flow channel groove and a particle.

By stabilizing a membrane-associated protein (enzyme or antibody) on the cell membrane mimetic structure layer of the MPC modified surface in a self organized manner, a protein (enzyme or antibody) can be immobilized on the surface of a substrate, a channel wall or a support such that the protein has an orientation.

Such a method described in Patent Document 1 is a method which is, when compared with a variety of conventional methods for immobilizing a protein, different from conventional methods in that in vivo behaviors are mimicked, and a new immobilization method which belongs to a new category which is a sort of a immobilization method by self organization of a protein for itself using any proteins as long as the protein has a membrane association. By this method, an increase in performance of a variety of applications (products) can be attained.

In the above described invention in the prior patent document 1, electron transfer in protein is an extremely effective technique from the viewpoint of immobilizing the orientation of an enzyme. However, in cases where an enzyme electrode is constructed by immobilizing a membrane-associated oxidoreductase, an attempt to attain a high efficiency of electron transfer pathway from the membrane-associated enzyme to the electrode "only by immobilization of enzyme" is described and in the Examples, only a general purpose carbon as a substrate is mentioned, and an approach of improving an ability of giving and receiving an electron in an electrode material used as the substrate was not addressed. An enzyme electrode has room for improvement in that the sensor can be optimized as a sensor which has a high efficiency of manufacturing, a high stability and a high usability because, generally, an enzyme electrode is greatly influenced by a method of manufacturing a substrate electrode or the shape of the electrode in its sensor performance.

PRIOR ART DOCUMENT

Patent Document

Patent Document 1: JP2006-322889A

DISCLOSURE OF THE INVENTION

An object of the present invention is to provide a sensor which has a high efficiency of manufacturing, a high responsiveness, a high long-term stability and a high usability. In order to attain the object, the present invention is
an electrochemical sensor comprising
a substrate,
an electrically conductive layer made of carbon particles which is disposed on the substrate,
a cell membrane mimetic structure layer containing an enzyme at least one of inside the cell membrane mimetic structure layer and on the interface of the cell membrane mimetic structure layer which is disposed on the electrically conductive layer.

By using the present invention, a protein such as oxidoreductase can be immobilized with high orientation, and therefore, fluctuation of an activity does not occur with a low enzyme level, and a desired activity can be expressed appropriately and cost-advantageously as well as a signal of an enzyme electrode can be more increased by an increase in the efficiency of electron transfer between enzyme and electrode. In addition, by immobilizing an enzyme such that the enzyme electrode has a membrane association in which in vivo behavior is mimicked, the enzyme can be immobilized more firmly on the surface of the electrode, thereby, surprisingly, improving a long-term stability as a sensor.

By using the present invention, the efficiency of manufacturing an electrochemical sensor can be remarkably improved by using carbon particles (carbon black) as a screen printing ink containing a binder and a solvent, performing a pattern printing on a substrate such as a resin by a screen printing method and forming an electrode, whereby the difference between the sensors can be made small.

Further, the electrochemical sensor of the present invention is expected to be highly adapted to an implantable continuous measurement sensor because a more minute electrochemical sensor can be manufactured since a sensor patterning by a screen printing method is possible; because an in vivo safety is improved by not using an additional mediator which is toxic for a living thing; and because the sensor has a long-term stability.

By the electrochemical sensor, an electrically conductive layer can be manufactured by filling carbon particles, and the response sensitivity to glucose can be evaluated simply.

In cases where an electrochemical sensor is constructed by immobilizing a membrane-associated oxidoreductase on an electrode by the present method, a high efficiency of electron transfer pathway of a membrane-associated enzyme can be attained while mimicking an in vivo behavior of the membrane-associated enzyme.

PREFERRED EMBODIMENTS OF THE INVENTION

Figure 1:
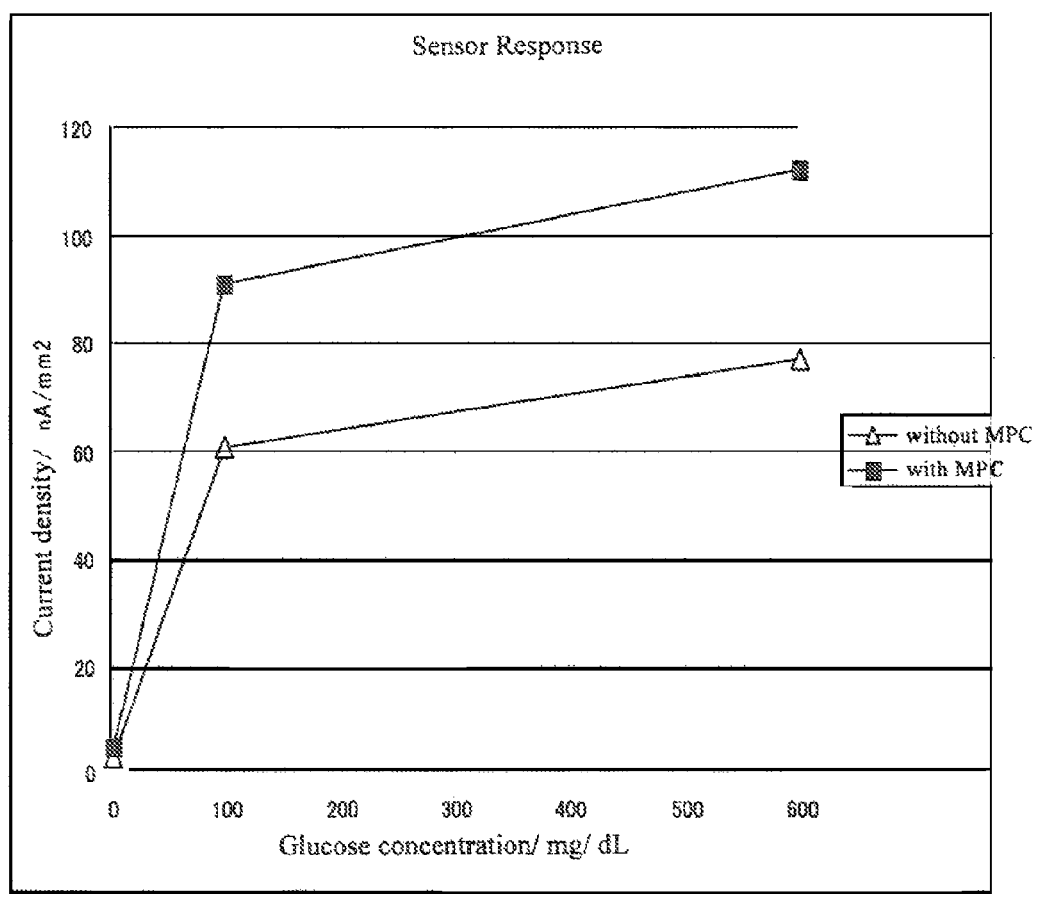
FIG. 1 is a graph showing the response sensitivity of an electrochemical sensor of the present invention in which the sensor was used to perform the quantification of glucose, in the case that BLACK PEARLS 2000 was used as carbon particles and a carbon containing electrically conductive layer was manufactured by screen printing.

The essential part of the present invention is the use of carbon black and the immobilization of an enzyme by using a cell membrane mimetic structure. The description thereof is as follows.

The above-mentioned cell membrane mimetic structure layer of the electrochemical sensor of the present invention is preferred to be a phospholipid membrane. The cell membrane mimetic structure layer is for immobilizing enzymes while mimicking in vivo behavior. The enzymes exist at least one of inside the cell membrane mimetic structure layer and on the interface of the cell membrane mimetic structure layer.

The phospholipid membrane of an electrochemical sensor of the present invention as the above-mentioned cell membrane mimetic structure layer is preferred to be 2-methacryloyloxyethyl phosphorylcholine (MPC) polymer. As the MPC polymer, those in which MPC alone is polymerized or those in which MPC is copolymerized with a hydrophobic monomer such as methacrylate (e.g. butyl methacrylate) can be used. The MPC polymer may also be those in which MPC is copolymerized with an anionic monomer or a cationic monomer. Such a cell membrane mimetic structure layer can be disposed by dispensing a drop of a solution containing the above-mentioned phospholipid polymer on an arbitrary portion (e.g. exposure portion enclosed by an insulating film) on a substrate such as an working electrode or counter electrode and then being subjected to drying. In the present invention, the disposition of a cell membrane mimetic structure layer includes the formation of a cell membrane mimetic structure layer.

The enzyme of the electrochemical sensor of the present invention is preferred to be a glucose dehydrogenase. Unlike a glucose oxidase, a glucose dehydrogenase does not mediate oxygen during a reaction, which has an advantage of not being influenced by, for example, an oxygen partial pressure in the test sample.

The glucose dehydrogenase of the electrochemical sensor of the present invention is preferred to be a glucose dehydrogenase which has a cytochrome as a subunit (hereinafter, also referred to as a "Cy-GDH"). When a glucose dehydrogenase which has a cytochrome as a subunit is used, it is not necessary to additionally use a mediator such as alkali metal ferricyanide. Here, the Cy-GDH used in the present invention refers to those containing at least an α-subunit having a glucose dehydrogenase activity and a cytochrome C having an electron transport function, and also includes those further containing a subunit other than the α-subunit or cytochrome C. Examples of such a Cy-GDH are disclosed in WO02/36779. The Cy-GDH described in the international application is one which is derived from a microorganism belonging to *Burkholderia cepacia*; in which the molecular weight thereof in a SDS-polyacrylamide gel electrophoresis under a reducing condition is about 60 kDa; in which FAD is contained as a cofactor as well as an α-subunit having a glucose dehydrogenase activity (the molecular weight thereof in a SDS-polyacrylamide gel electrophoresis under a reducing condition is about 43 kDa) and a cytochrome C having an electron transport function are contained. The Cy-GDH of the present invention also includes those obtained by utilizing a transformant into which a gene encoding a Cy-GDH obtained from a microorganism belonging to *Burkholderia cepacia* is transferred.

The above-mentioned enzyme of the electrochemical sensor of the present invention is preferred to be formed on the above-mentioned cell membrane mimetic structure layer in such a state that the enzyme is self-organized with respect to the cell membrane mimetic structure layer. For example, since a Cy-GDH derived from a microorganism belonging to *Burkholderia cepacia* is a membrane-associated protein, which originally exists on a cell membrane, when such a Cy-GDH is applied on the membrane, a cell membrane mimetic structure layer can be formed by immobilizing a Cy-GDH on the membrane in such a state that the Cy-GDH is self-organized with respect to the cell membrane mimetic structure layer and the Cy-GDH has an orientation in the same manner as in the case where the Cy-GDH is in the cell membrane. Such a self-organized immobilization of an enzyme is not limited to a Cy-GDH derived from a microorganism belonging to *Burkholderia cepacia*, and can be attained when a membrane associated enzyme which exists in a cell membrane is used.

In addition to carbon particles, binders can be contained on the above-mentioned electrically conductive layer of the electrochemical sensor of the present invention. By taking this constitution, carbon particles (carbon black) can be prepared as a screen printing ink containing a binder and a solvent in a manufacturing process. For this reason, by forming an electrode by a pattern printing on a substrate such as resins using a screen printing method, the efficiency of manufacturing an enzyme electrode can be remarkably improved whereby the difference between the sensors can be made small. Solvents contained in the manufacturing process are vaporized by drying, and is not contained in the constitution of an enzyme electrode.

As the binder for disposing the above-mentioned electrically conductive layer with carbon particles, a variety of resin binders which can be dissolved or dispersed in a solvent in a manufacturing process can be used, and particularly butyral resin binder and polyester resin binder can be preferably used. As the solvent, Carbitol acetate (diethylene glycol monoethyl ether acetate), isophorone and cyclohexane can be preferably used. In the present invention, the disposition of an electrically conductive layer includes the formation of an electrically conductive layer.

In the electrochemical sensor of the present invention, the above-mentioned electrically conductive layer and the above-mentioned cell membrane mimetic structure layer may be combined. That is, a layer in which the above-mentioned electrically conductive layer and the above-mentioned cell membrane mimetic structure layer are combined can be formed by preparing and mixing in advance a screen printing ink for forming an electrically conductive layer containing carbon particles and a solution containing a phospholipid polymer for forming a cell membrane mimetic structure layer, and dispensing a drop of the mixed solution on a substrate such as a working electrode and a counter electrode and drying. A layer combined in such a way has a great advantage in manufacturing.

Further, the final enzyme electrode can be manufactured in one step by mixing, in advance, a membrane-associated enzyme into the above-mentioned mixture of the screen printing ink and the phospholipid polymer, and by performing pattern printing on the substrate by a screen printing method.

A method for manufacturing an electrochemical sensor of the present invention comprising disposing on a substrate an electrically conductive layer made of carbon particles, disposing on the electrically conductive layer a cell membrane mimetic structure layer, and immobilizing an enzyme on the cell membrane mimetic structure layer.

Immobilization of a membrane-associated enzyme on the cell membrane mimetic structure layer (i.e., self-organizing immobilization) can be performed, for example, such that a substrate, on the exposed portion of which a cell membrane mimetic structure layer is formed, is immersed in an enzyme solution containing the membrane-associated enzyme, and then dried, or such that the above-mentioned enzyme solution is spayed on the cell membrane mimetic structure layer, and then dried. When a membrane-associated enzyme is immobilized on the cell membrane mimetic structure layer in a self-organized way, the membrane-associated enzyme is formed inside and/or on the interface of the cell membrane mimetic structure layer with orientation. When the enzyme is Cy-GDII, that is, a glucose dehydrogenase which has cytochrome as a subunit, the enzyme is immobilized on a cell membrane mimetic structure layer such that an active site of an α-subunit having a glucose dehydrogenase activity is immobilized on the surface layer of an enzyme electrode which is closest to a test sample while the cytochrome is closest to or in contact with the electrode.

A Cy-GDH derived from a microorganism belonging to *Burkholderia cepacia* is a membrane-associated protein. Since the above-mentioned Cy-GDH derived from a microorganism originally exists in a cell membrane, when such a Cy-GDH is used, the Cy-GDH can be immobilized in such a state that the Cy-GDH is self-organized with respect to the cell membrane mimetic structure layer and the Cy-GDH has an orientation in the same manner as in the case where Cy-GDH is in the cell membrane. Such a self-organized immobilization of an enzyme is not limited to a Cy-GDH derived from a microorganism belonging to *Burkholderia cepacia*, and can be attained when a membrane associated enzyme which exists in a cell membrane is used.

In the method for manufacturing an electrochemical sensor of the present invention, as the phospholipid polymer, those in which silane coupling agent is introduced can also be used. In cases where a silane coupling agent is introduced in a cell membrane mimetic substance in such a manner, a cell membrane mimetic structure layer can be formed on an electrically conductive layer by reacting with OH groups on the electrically conductive layer in a step of disposing the cell membrane mimetic structure layer, and at this time, the affinity of phospholipid polymer to the exposed portion of the electrically conductive layer can be enhanced.

In the method for manufacturing an electrochemical sensor of the present invention, when those in which a silane coupling agent is introduced are used as a phospholipid polymer, by performing a hydrophilization treatment on the electrically conductive layer in advance and forming at the hydrophilized site a cell membrane mimetic structure layer in which a silane coupling agent is introduced, this hydrophilic group is bound to the silane coupling agent and a phospholipid polymer can be immobilized on the exposed portion more firmly.

By forming a cell membrane mimetic structure layer after a hydrophilization treatment by a VUV treatment on the surface of an electrically conductive layer, a phospholipid polymer can be immobilized more firmly.

Here, the amount of silane coupling agent in the phospholipid polymer is, for example, 10 to 500 parts by weight based on 100 parts by weight of the polymer component. Examples of the silane coupling agent include tetraethoxy silane, vinyl trichlorosilane, vinyl tris(2-methoxyethoxy) silane, γ-metacryloxypropyltrimethoxysilane, γ-metacryloxypropyltriethoxysilane, β-(3,4-epoxycyclohexyl)ethyltrimethoxysilane, γ-glycidoxypropyltriethoxysilane, γ-amino propyltriethoxysilane, N-phenyl-γ-amino propyltrimethoxysilane, γ-chloro propyltrimethoxysilane and γ-mercapto propyltrimethoxysilane, and these silane coupling agents may be used alone or a plurality of these may be used in combination.

(Selection of Material of the Electrically Conductive Layer)

The present inventors searched for preferred materials for improving the efficiency of exchange of electrons from an enzyme to an electrode to discover that, taken into account the particle size and specific surface area of electrically conductive particles, a combination of an electrically conductive layer made of a material (carbon particle) in which not only a primary particle size but also a secondary particle size which is in an association state is small, the density is small and the surface area is remarkably large, and a cell membrane mimetic structure layer is preferred. In particular, it is probed that a carbon particle in which the primary particle size is 30 nm to 100 nm and the specific surface area is 200 $m^2/g$ to 1,400 $m^2/g$ is preferred in the manufacturing of a biosensor. Examples of the carbon particle include carbon black, and representative examples of carbon black which is easily-available include BLACK PEARLS (trademark; manufactured by Cabot Corporation) and Ketjen Black (trademark; manufactured by AkzoNobel Chemicals Co., Ltd.). Examples of a measuring method of the particle size and specific surface area include a measurement by a transmission electron microscope and a BET specific surface area method.

(Optimization of a Method for Manufacturing a Sensor by Using a Screen Ink for an Electrically Conductive Layer Material)

When the above-mentioned carbon material is used, since it is possible to mix a mineral oil or the like into a carbon material which is a powder to make a paste, the adherence thereof is poor and the structure of a sensor tends to be unstable. Accordingly, in the present invention, it is preferred to manufacture a screen printing ink by making the above-mentioned carbon particles impregnated with a binder and a solvent. By pattern printing the ink on a substrate such as resins by a screen printing method and forming an electrode by printing, the efficiency in the manufacturing process extremely improves.

(Optimization of a Method for Manufacturing a Sensor by Filling a Carbon Material)

In the present invention, the response sensitivity to glucose can also be simply evaluated by manufacturing an electrically conductive layer by filling a paste obtained by adding liquid paraffin to the above-mentioned carbon particles and using the layer for an electrochemical sensor.

(Immobilization of the Orientation of Enzyme on the Electrically Conductive Layer Material)

On the above-mentioned electrically conductive layer, a cell membrane mimetic structure (phospholipid) is formed by using MPC or the like to modify the surface of the electrode. Further, an enzyme electrode (electrochemical sensor) is manufactured by, for example, immersing the above-described modified electrode into a membrane-associated enzyme solution or dispensing the membrane-associated enzyme solution on the surface of the modified electrode and making a working electrode by immobilizing an enzyme on the above-mentioned modified electrode. An electrode system is usually composed of a working electrode, a counter electrode and reference electrode.

EXAMPLE 1

In Example 1, an examination was carried out on the response sensitivity and stability of an electrochemical sensor on which an electrically conductive layer was formed by a screen printing method in which BLACK PEARLS was used as carbon particles and this BLACK PEARLS was contained on the surface of the substrate. The effect of application of the electrochemical sensor of the present invention is shown as a data in which a glucose dehydrogenase (Cy-GDH) from a microorganism belonging to *Burkholderia cepacia* which has cytochrome as a subunit is used as one example.

As the electrode system,
a working electrode: enzyme-immobilized electrode,
a counter electrode: platinum electrode, and
a reference electrode: silver/silver chloride electrode were used.

For the above-mentioned enzyme-immobilized electrode which is a working electrode, an electrochemical sensor using a cell membrane mimetic structure layer of the present invention, and, as a reference example, an electrochemical sensor with a conventional absorption type enzyme-immobilized electrode in which MPC is not mediated and an enzyme is directly adsorbed on the electrically conductive layer were used.

In the present invention, on the surface of polyimide substrate, an electrically conductive layer (carbon layer), cell membrane mimetic structure layer (phospholipid polymer layer) and enzyme-immobilized membrane (Cy-GDH layer) were formed according to the present invention.

As the carbon particles, BLACK PEARLS 2000 (hereinafter, referred to as BP) having a particle diameter of 50 nm, a specific surface area of 1400 m$^2$/g and a porosity of 60 vol % was prepared. Based on the weight ratio, 40% of BP, 40% of polyester resin as a binder and 20% of isophorone as a solvent were mixed to obtain a printing ink. The ink was printed on the surface of polyimide substrate such that the thickness of the ink is 10 μm and dried at 150° C. for 30 minutes to obtain an electrically conductive layer.

A phospholipid polymer layer was formed by a hydrophilization treatment by a VUV treatment on the surface of the electrically conductive layer and thereafter, applying a MPC polymer solution on the surface of the electrically conductive layer and drying. The VUV treatment was performed by irradiating an excimer laser having a wavelength of 172 nm on the surface of the electrically conductive layer for 180 seconds with an irradiation distance of 1 mm in the air using "MECL-M3-750" (manufactured by MD Excimer Co., Ltd.). As the phospholipid polymer solution, a MPC polymer into which a silane coupling agent is introduced (Product name: "LIPIDURE CR-1702"; manufacture by NOF CORPORATION) was used.

A Cy-GDH layer was formed by immersing an electrically conductive layer on which a phospholipid polymer layer was formed into a Cy-GDH solution for 10 minutes. The concentration of the Cy-GDH in the Cy-GDH solution was made 100 U/μL at the activity baseline. By using the manufactured enzyme electrode as a working electrode, Pt as a counter electrode and Ag/AgCl reference electrode as a reference electrode, an enzyme electrode system using a cell membrane mimetic structure layer of the present invention was constructed.

On the other hand, a reference Example 1 was formed in the same manner as in Example 1 except that the phospholipid polymer layer was not formed on the working electrode, and used as a conventional absorption type enzyme-immobilized electrode system in which MPC was not mediated and an enzyme was directly adsorbed on the electrically conductive layer.

By using these electrode systems, without using an additional mediator, the response sensitivity to glucose was examined by a chronoamperometry in which 600 mV of potential difference is applied to the electrode systems. In the measurement of the response sensitivity, each of the enzyme electrode systems (working electrode/counter electrode/reference electrode) in Example 1 and the reference Example 1 was immersed in a 0.1 M phosphate buffer solution (pH=7.0). Then, a constant voltage (600 mV vs. Ag/AgCl) was applied to each of the enzyme electrodes while 2.0 M glucose aqueous solution was continued to be dropped in the solution, and the constant current density (nA/mm$^2$) at a final concentration of glucose of 100 mg/dl and 600 mg/dl was measured. The constant current density corresponds to the response sensitivity. The result is shown in FIG. 1. As also shown in FIG. 1, the electrochemical sensor with an enzyme-immobilized electrode which is a cell membrane mimetic structure of the present invention in which an MPC is mediated was confirmed to have a higher response sensitivity than that of the electrochemical sensor of the comparative Example with an absorption type enzyme-immobilized electrode in which an MPC is not mediated.

Figure 2:
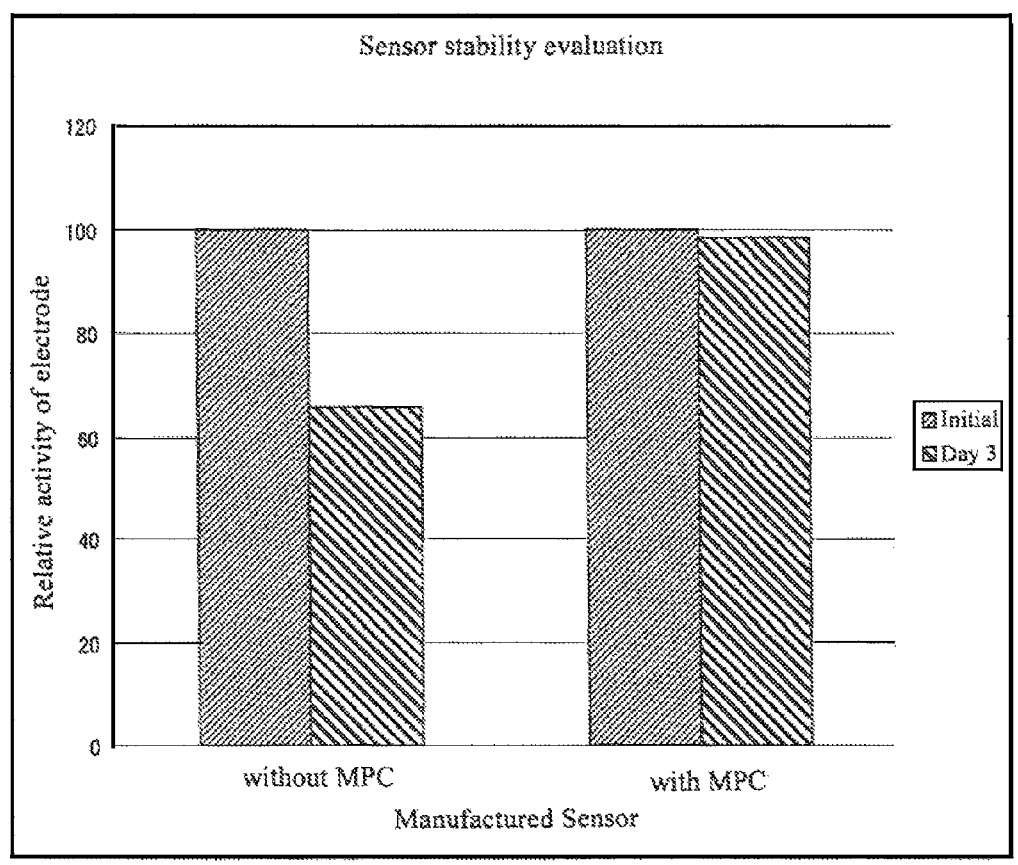
FIG. 2 is a graph in which the stability of an electrochemical sensor of the present invention which was used continuously was evaluated, in the case that BLACK PEARLS 2000 was used as carbon particles and a carbon containing electrically conductive layer was manufactured by screen printing.

Then, the stability of an electrode system of the present invention was evaluated. In the method of evaluating the stability, the initial response sensitivity of each of the enzyme electrode systems in Example 1 and the reference Example 1 was measured. Next, the response sensitivity of each of the enzyme electrode systems in Example 1 and the reference Example 1 after immersing the systems into a 0.1 M phosphate buffer solution (pH=7.0) at room temperature for 3 days was measured. The measuring method of the response sensitivity was performed in the same conditions as in the above-mentioned examination of the response sensitivity. The result is shown in FIG. 2. A graph in FIG. 2 shows a relative activity to the initial value (the final concentration of glucose was 100 mg/dl). As the result, the electrochemical sensor with an enzyme-immobilized electrode in which an MPC is mediated was confirmed to have a higher stability than that of the electrochemical sensor with an absorption type enzyme-immobilized electrode in which an MPC is not mediated.

EXAMPLE 2

In Example 2, Ketjen Black is used as carbon particles and the stability of an electrochemical sensor on which an electrically conductive layer is formed on the surface of the substrate by a screen printing method including this Ketjen Black was examined. The effect of application of the electrochemical sensor of the present invention is shown as a data in which a glucose dehydrogenase from a microorganism belonging to *Burkholderia cepacia* which has cytochrome as a subunit is used as one example.

As the electrode system,
a working electrode: enzyme-immobilized electrode,
a counter electrode: platinum electrode, and
a reference electrode: silver/silver chloride electrode were used.

For the above-mentioned enzyme-immobilized electrode which is a working electrode, an electrochemical sensor using a cell membrane mimetic structure layer of the present invention, and, as a reference example, an electrochemical sensor with a conventional absorption type enzyme-immobilized electrode in which MPC is not mediated and an enzyme is directly adsorbed on the electrically conductive layer were used.

In the present invention, on the surface of polyimide substrate, an electrically conductive layer (carbon layer), cell membrane mimetic structure layer (phospholipid polymer layer) and enzyme-immobilized membrane (Cy-GDH layer) were formed according to the present invention.

As the carbon particles, Ketjen Black EC600JD (hereinafter, referred to as KB) having a particle diameter of 34 nm, a specific surface area of 1270 $m^2$/g and a porosity of 80 vol % was prepared. Based on the weight ratio, 40% of KB, 40% of polyester resin as a binder and 20% of isophorone as a solvent were mixed to obtain a printing ink. The ink was printed on the surface of polyimide substrate such that the thickness of the ink is 10 μm and dried at 150° C. for 30 minutes to obtain an electrically conductive layer.

A phospholipid polymer layer was formed on the surface of the above-mentioned electrically conductive layer by immersing the layer into a MPC polymer solution (0.05% MPC aqueous solution (0.1 M phosphate buffer solution is used as a solvent)) for six hours. As the phospholipid polymer solution, a MPC polymer into which a silane coupling agent is introduced (Product name: "LIPIDURE CR-1702"; manufacture by NOF CORPORATION) was used.

A Cy-GDH layer was formed by rinsing with distilled water and thereafter immersing an electrically conductive layer on which a phospholipid polymer layer was formed into a Cy-GDH solution (1 mg/ml of Cy-GDH solution) overnight. The concentration of the Cy-GDH in the Cy-GDH solution was made 100 U/μL at the activity baseline. By using the manufactured enzyme electrode as a working electrode, Pt as a counter electrode and Ag/AgCl reference electrode as a reference electrode, an enzyme electrode system using a cell membrane mimetic structure layer of the present invention was constructed.

On the other hand, a reference Example 2 was formed in the same manner as in Example 2 except that the phospholipid polymer layer was not formed on the working electrode, and used as a conventional absorption type enzyme-immobilized electrode system in which a cell membrane mimetic structure layer was not mediated and an enzyme was directly adsorbed on the electrically conductive layer.

Figure 3:
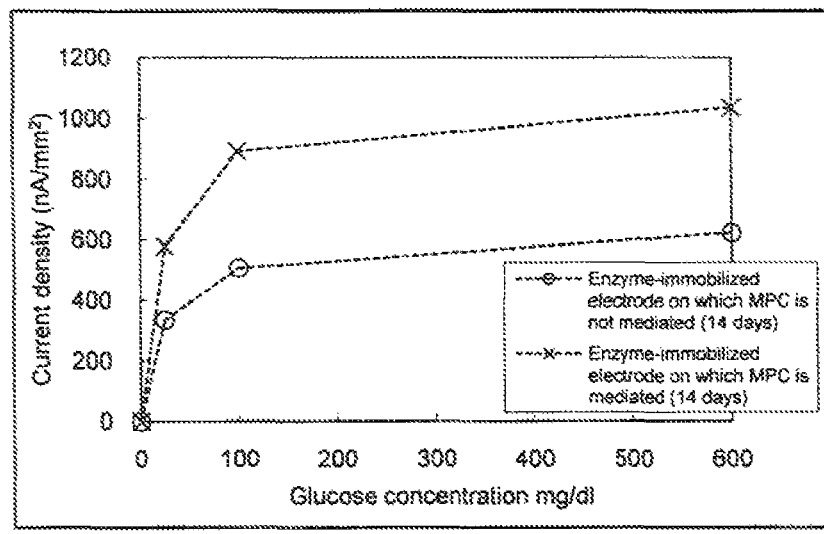
FIG. 3 is a graph showing the response sensitivity of an electrochemical sensor of the present invention in which the sensor was used to perform the quantification of glucose, in the case that Ketjen Black was used as carbon particles and a carbon containing electrically conductive layer was manufactured by screen printing.

By using these electrode systems, without using an additional mediator, the response sensitivity to glucose was examined by a chronoamperometry in which 600 mV of potential difference is applied to the electrode systems. In the measurement of the response sensitivity, each of the enzyme electrode systems (working electrode/counter electrode/reference electrode) in Example 2 and the reference Example 2 was immersed in a 0.1 M phosphate buffer solution (pH=7.0). Then, a constant voltage (600 mV vs. Ag/AgCl) was applied to each of the enzyme electrodes while 2.0 M glucose aqueous solution was continued to be dropped in the solution, and the constant current density (nA/$mm^2$) at a final concentration of glucose of 25 mg/dl, 100 mg/dl and 600 mg/dl was measured. The constant current density corresponds to the response sensitivity. The result is shown in FIG. 3. As also shown in FIG. 3, the electrochemical sensor with an enzyme-immobilized electrode which is a cell membrane mimetic structure of the present invention in which an MPC is mediated was confirmed to have a higher response sensitivity than that of the electrochemical sensor of the comparative Example 2 with an absorption type enzyme-immobilized electrode in which an MPC is not mediated.

EXAMPLE 3

In Example 3, Ketjen Black is used as carbon particles and the stability of an electrochemical sensor on which an electrically conductive layer is formed on the surface of the substrate by a method of filling this Ketjen Black was examined. The effect of application of the electrochemical sensor of the present invention is shown as a data in which a glucose dehydrogenase from a microorganism belonging to *Burkholderia cepacia* which has cytochrome as a subunit is used as one example.

As the electrode system,
a working electrode: enzyme-immobilized electrode,
a counter electrode: platinum electrode, and
a reference electrode: silver/silver chloride electrode were used.

For the above-mentioned enzyme-immobilized electrode which is a working electrode, an electrochemical sensor using a cell membrane mimetic structure layer of the present invention, and, as a reference example, an electrochemical sensor with a conventional absorption type enzyme-immobilized electrode in which MPC is not mediated and an enzyme is directly adsorbed on the electrically conductive layer were used.

In the present invention, on the surface of polyimide substrate, an electrically conductive layer (carbon layer), cell membrane mimetic structure layer (phospholipid polymer layer) and enzyme-immobilized membrane (Cy-GDH layer) were formed according to the present invention.

As the carbon particles, Ketjen Black EC600JD (hereinafter, referred to as KB) having a particle diameter of 34 nm, a specific surface area of 1270 $m^2$/g and a porosity of 80 vol % was prepared. To 60 mg of this powder, 100 μL of liquid paraffin was added and well mixed to be processed to a paste. This paste was filled in a base electrode for making a paste electrode having a diameter of 3 mm (CPE carbon paste electrode manufactured by BAS Co., Ltd.) and the electrode was compressed to have a thickness of 2 mm to obtain an electrically conductive layer.

A phospholipid polymer layer was formed on the surface of the above-mentioned electrically conductive layer by immersing the layer into a MPC polymer solution (0.05% MPC aqueous solution (0.1 M phosphate buffer solution is used as a solvent)) for six hours. As the phospholipid polymer solution, a MPC polymer into which a silane coupling agent is introduced (Product name: "LIPIDURE CR-1702"; manufacture by NOF CORPORATION) was used.

A Cy-GDH layer was formed by rinsing with distilled water and thereafter immersing an electrically conductive layer on which a phospholipid polymer layer was formed into a Cy-GDH solution (1 mg/ml of Cy-GDH solution) overnight. The concentration of the Cy-GDH in the Cy-GDH solution was made 100 U/μL at the activity baseline. By using the manufactured enzyme electrode as a working electrode, Pt as a counter electrode and Ag/AgCl reference electrode as a reference electrode, an enzyme electrode system using a cell membrane mimetic structure layer of the present invention was constructed.

On the other hand, a reference Example 3 was formed in the same manner as in Example 3 except that the phospholipid polymer layer was not formed on the working electrode, and a conventional absorption type enzyme-immobilized electrode system in which a cell membrane mimetic structure layer was not mediated and an enzyme was directly adsorbed on the electrically conductive layer were used.

Figure 4:
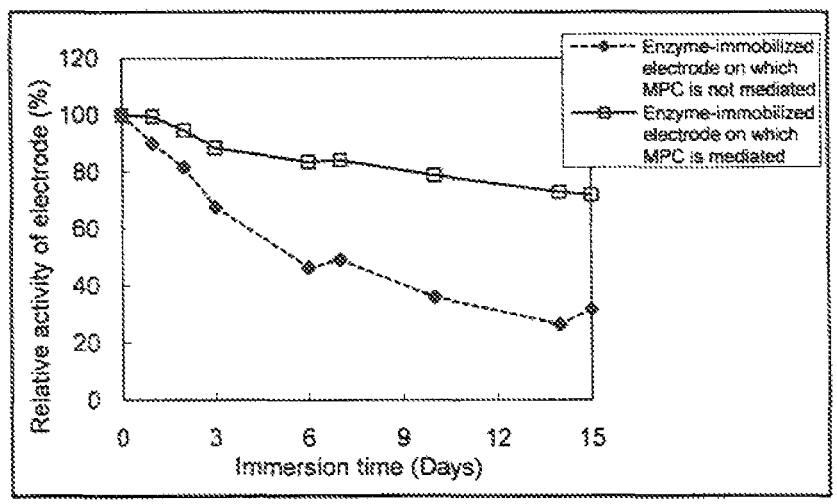
FIG. 4 is a graph in which the stability of an electrochemical sensor of the present invention which was used continuously was evaluated, in the case that Ketjen Black was used as carbon particles and an electrically conductive layer was manufactured by filling carbon particles.

The stability of an electrode system of the present invention was evaluated. In the method of evaluating the stability, the initial response sensitivity of each of the enzyme electrode systems in Example 3 and the reference Example 3 was measured. Next, the response sensitivity of each of the enzyme electrode systems in Example 3 and the reference Example 3 after immersing the systems into a 0.1 M phosphate buffer solution (pH=7.0) at room temperature for 1, 2, 3, 6, 7, 10, 14, 15 days was measured. The measuring method of the response sensitivity was performed in the same conditions as in the examination of the response sensitivity shown in Example 1. The result is shown in FIG. 4. A graph in FIG. 4 shows a relative activity to the initial value (the final concentration of glucose was 100 mg/dl). As the result, the electrochemical sensor with an enzyme-immobilized electrode in which an MPC is mediated was confirmed to have a higher stability than that of the electrochemical sensor with an absorption type enzyme-immobilized electrode in which an MPC is not mediated.

The invention claimed is:

1. An electrochemical sensor comprising
   a substrate,
   an electrically conductive layer made of carbon particles,
   a cell membrane mimetic structure layer containing an enzyme at least one of inside the cell membrane mimetic structure layer and on the interface of the cell membrane mimetic structure layer,
   wherein the electrically conductive layer and the cell membrane mimetic structure layer are combined and the combined layer is disosed on the substrate.

2. The electrochemical sensor according to claim 1, wherein the cell membrane mimetic structure layer is a phospholipid membrane.

3. The electrochemical sensor according to claim 2, wherein the phospholipid membrane is a 2-methacryloyloxyethyl phosphorylcholine polymer.

4. The electrochemical sensor according to claim 1, wherein the enzyme is a glucose dehydrogenase.

5. The electrochemical sensor according to claim 1, wherein the enzyme is immobilized on the cell membrane mimetic structure layer in such a state that the enzyme is self-organized with respect to the cell membrane mimetic structure layer.

6. The electrochemical sensor according to claim 1, wherein the carbon particles have a primary particle size of 100 nm or smaller and a specific surface area of 200 $m^2$/g or larger.

7. The electrochemical sensor according to claim 1, wherein the carbon particles are Ketjen Black™ or BLACK PEARLS™.

8. The electrochemical sensor according to claim 1, wherein the combined layer is formed by screen printing the carbon particles.

9. A method for manufacturing an electrochemical sensor comprising
   preparing and mixing an ink for forming an electrically conductive layer containing carbon particles and a solution containing a phospholipid polymer for forming a cell membrane mimetic structure layer,
   dispensing a drop of the mixed solution on a substrate and drying, and
   immobilizing an enzyme on the cell membrane mimetic structure layer,
   wherein the electrically conductive layer and the cell membrane mimetic structure layer are combined.

10. The method according to claim 9, wherein the cell membrane mimetic structure layer is a phospholipid membrane.

11. The method according to claim 10, wherein the phospholipid membrane is 2-methacryloyloxyethyl phosphorylcholine polymer.

12. The method according to claim 9, wherein the enzyme is a glucose dehydrogenase.

13. The method according to claim 9, wherein the enzyme is immobilized on the cell membrane mimetic structure layer in such a state that the enzyme is self-organized with respect to the cell membrane mimetic structure layer.

14. The method according to claim 9, wherein the carbon particles have a primary particle size of 100 nm or smaller and a specific surface area of 200$m^2$/g or larger.

15. The method according to claim 9, wherein the carbon particles are Ketjen Black™ or BLACK PEARLS™.

16. The method according to claim 9, wherein the combined layer is formed by screen printing the carbon particles.

* * * * *